US006517813B1

(12) United States Patent
Weitschies et al.

(10) Patent No.: US 6,517,813 B1
(45) Date of Patent: *Feb. 11, 2003

(54) DEVICE AND PROCESS FOR SEPARATING MAGNETIC MATERIALS FROM PHARMACEUTICAL PREPARATIONS, THEIR STARTING OR INTERMEDIATE PRODUCTS, AS WELL AS AGENTS THAT ARE PRODUCED WITH THE AID OF SAID DEVICE

(75) Inventors: Werner Weitschies, Berlin (DE); Thomas Rheinländer, Berlin (DE); Wolfgang Ebert, Mahlow (DE); Bernard Better, Berlin (DE)

(73) Assignee: Schering AG, Berlin (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/904,765

(22) Filed: Aug. 1, 1997

(30) Foreign Application Priority Data

Aug. 5, 1996 (DE) .......................................... 196 32 416

(51) Int. Cl.⁷ ................................................ A61B 5/055
(52) U.S. Cl. ................... 424/9.3; 424/9.322; 424/9.323
(58) Field of Search ............................ 424/9.32, 9.322, 424/9.323, 646, 648; 600/420

(56) References Cited

U.S. PATENT DOCUMENTS

| 3,817,389 A | | 6/1974 | Weichselbaum ............. 210/448 |
| 4,707,255 A | | 11/1987 | Fjeldsend, Jr. |
| 5,045,304 A | * | 9/1991 | Schneider et al. ............. 424/9 |
| 5,160,726 A | * | 11/1992 | Josephson et al. ............ 424/9 |
| 5,225,282 A | * | 7/1993 | Chagnon et al. ............ 428/407 |
| 5,268,165 A | * | 12/1993 | Hedlund et al. ............... 424/9 |
| 5,328,681 A | | 7/1994 | Kito et al. |
| 5,411,730 A | * | 5/1995 | Kirpotin et al. ......... 424/9.322 |
| 5,411,863 A | * | 5/1995 | Miltenyi ........................ 435/6 |
| 5,424,419 A | | 6/1995 | Hasegawa et al. |
| 5,766,572 A | | 6/1998 | Hasegawa et al. |
| 5,804,162 A | * | 9/1998 | Kabalnov et al. .......... 424/9.51 |
| 5,855,868 A | | 1/1999 | Fahlvik |
| 5,916,539 A | * | 6/1999 | Pilgrimm ................. 424/9.322 |
| 6,048,515 A | | 4/2000 | Kresse et al. |
| 6,207,134 B1 | * | 3/2001 | Fahlvik et al. ........... 424/9.322 |

FOREIGN PATENT DOCUMENTS

| EP | 0 186 612 B2 | 1/1995 |
| EP | 0 670 185 | 9/1995 |
| EP | 0 543 020 B1 | 12/1997 |
| EP | 0 656368 B1 | 4/1999 |
| EP | 0 525 199 B1 | 5/1999 |
| WO | WO90/01899 | 3/1990 |
| WO | 90/07380 | 7/1990 |
| WO | WO96/04017 | 2/1996 |
| WO | WO98/05430 | 2/1998 |

OTHER PUBLICATIONS

Patent Abstracts of Japan, vol. 011, No. 185 (C–428) (Jun. 13, 1987).
Patent Abstracts of Japan, vol. 010, No. 112 (C–342) (Apr. 25, 1986).
Abstract of EPO 439983, Aug. 1991.
Abstract of Japanese 165334, 1991.
Abstract of German DE 4309333, Sep. 1994.
English Translation of WO 96/04017, 1996.

* cited by examiner

*Primary Examiner*—Michael G. Hartley
(74) *Attorney, Agent, or Firm*—Millen, White Zelano & Branigan, P.C.

(57) ABSTRACT

The invention relates to a device for magnetic separation of pharmaceutical preparations, their starting or intermediate products that contain a separation space, in which a magnetic gradient field prevails and which has an inlet and an outlet, whereby the device is embodied in the form of an attachment filter for injection instruments or infusion instruments.

8 Claims, 8 Drawing Sheets

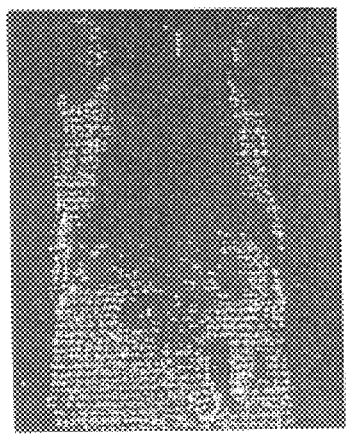 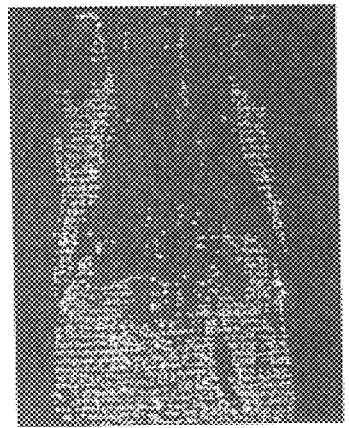 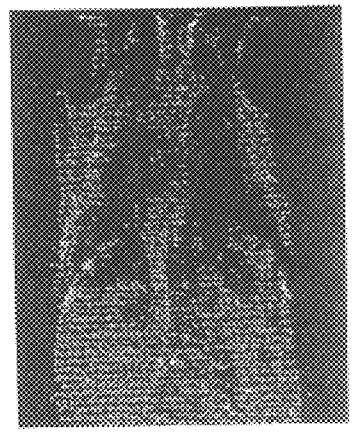
FIG. 6a
precontrast
FIG. 6b
1 minute p.i.
FIG. 6c
15 minutes p.i.

precontrast 1 minute p.i.

30 minutes p.i.

 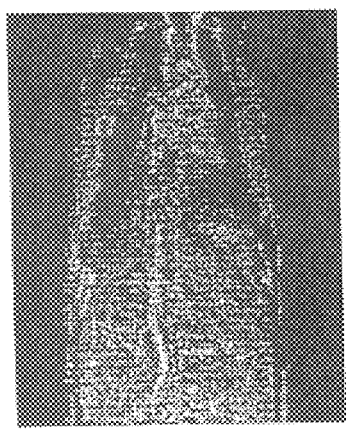 
FIG. 8a
precontrast
FIG. 8b
1 minute p.i.
FIG. 8c
30 minutes p.i.

DEVICE AND PROCESS FOR SEPARATING MAGNETIC MATERIALS FROM PHARMACEUTICAL PREPARATIONS, THEIR STARTING OR INTERMEDIATE PRODUCTS, AS WELL AS AGENTS THAT ARE PRODUCED WITH THE AID OF SAID DEVICE

The invention relates to the object that is characterized in the claims, i.e., a device for magnetic separation of pharmaceutical preparations, their starting or intermediate products that contain a separation space, in which a magnetic gradient field prevails and which has an inlet and an outlet, process for separating magnetic materials from pharmaceutical preparations, and agents that are produced with the aid of the device according to the invention and the process according to the invention.

In pharmaceutical preparations, foreign particles in the form of metallic particulate contaminants can result from production operations with metal tools or in metal containers or by injection instruments. For the protection of patients, therefore, the pharmacopeia stipulate the maximum limits, weighted according to particle size, for the number of foreign particles for pharmaceutical preparations that are to be administered parenterally, here especially in the case of infusions. These foreign particles are frequently ferromagnetic, ferrimagnetic, superparamagnetic or paramagnetic compounds.

Naturally occurring ferromagnetic contaminants of a starting substance can be separated according to a process that is described in U.S. Pat. No. 4,119,700. Here, the ferromagnetic contaminants are separated with the aid of a magnetic field. Processes for magnetic separation of biological materials are known from laid-open specifications WO 90/07380 and WO 83/02405. Laid-open specification WO 90/07380 describes a device in which a separation space is surrounded by a permanent magnet and which has an inlet and an outlet.

In the case of pharmaceutical preparations, the number of foreign particles to date is reduced if at all possible by processes of adsorption filtration or membrane filtration. Especially in the case of contaminants that are produced by user actions, such as, e.g., spraying pharmaceutical agents into infusion containers, however, it is difficult to reduce the number of foreign particles since correspondingly small-pore membrane filters often can be operated only with additional mechanical pressure. In most cases, filter inserts in infusion instruments therefore have pore sizes of several micrometers, which, however, lead to unsatisfactory retention rates for foreign particles. In the case of particulate pharmaceutical preparations, such as, e.g., parenteral fat emulsions or crystal suspensions as depot dosage forms, separating foreign particles by membrane or adsorption filtration is generally not possible at all.

The object of this invention was therefore to develop a device that makes it possible to separate magnetic particles, such as, e.g., metal contaminants, quickly and simply from pharmaceutical preparations and to simplify the separation process to such an extent that it can be done by the user himself.

This object is achieved by this invention.

A device for magnetic separation of pharmaceutical preparations, their starting or intermediate products that contain a separation space, in which a magnetic gradient field prevails and which has an inlet and an outlet, was developed that is characterized by the following feature: the device is designed in the form of an attachment filter for injection instruments or infusion instruments.

The device makes it possible to separate all compounds that are ferromagnetic, ferrimagnetic, superparamagnetic, or paramagnetic.

The gradient field that is used for separation has to be considerably stronger than the gradient of the natural field. The selection of the suitable gradient field depends on the magnetic moment of the substance that is to be separated. To separate paramagnetic compounds from diamagnetic pharmaceutical preparations, high-gradient fields are necessary.

To separate the undesirable magnetic compounds, the respective pharmaceutical preparation or its starting or intermediate product is directed through the device and thus through a magnetic gradient field. The higher the gradient of the magnetic gradient field, the stronger the force that acts on the paramagnetic, ferrimagnetic, superparamagnetic, or ferromagnetic contaminants. Pharmaceutical agents and pharmaceutical adjuvants (such as, for example, water) are generally diamagnetic and therefore experience a force that is very low in comparison to the paramagnetic, ferrimagnetic, superparamagnetic, or ferromagnetic contaminants; moreover, said force does not cause them to travel in the direction of the gradient but rather repels them. To separate magnetic contaminants from diamagnetic preparations, therefore, in contrast to filtration through small-pore filters (e.g., 0.22 $\mu$m membrane filter), no special pressure generally needs to be exerted in the separation according to the invention in the magnetic gradient field; generally the force of gravity or hydrostatic pressure is sufficient.

With the device according to the invention, the separation of the undesirable magnetic particles is carried out with the aid of a flow process. In the case of flow processes, in contrast to static processes, the flow rate has to be matched to the magnetic moments of the ferromagnetic, ferrimagnetic, or superparamagnetic substances that are to be separated and the field gradients that are applied.

The embodiment of the device according to the invention can be implemented in different ways. The magnetic gradient field in the separation space can be generated by, for example, a permanent magnet or an electromagnet that is attached outside the separation space. To increase the locally effective gradient of the magnetic field, it can be very helpful in this case for the separation space to consist of paramagnetic or soft-magnetic material and/or to contain paramagnetic or preferably soft-magnetic material.

The magnetic gradient field in the separation space can, however, also be generated by a permanent-magnetic material which forms the separation space or is found in a separation space.

In addition, the magnetic gradient field in the separation space can be generated by a conductor through which the current flows and which is located either in the separation space or surrounds the separation space. In both the above-mentioned cases, it can again be very helpful for the separation space to consist of paramagnetic or soft-magnetic material and/or to contain paramagnetic or preferably soft-magnetic material.

Soft-magnetic substances are preferably soft-magnetic iron or steel, especially in the form of fine shot (e.g., balls a few millimeters in diameter) or frits or in the form of wire (such as, e.g., steel wool, nets, or sieves).

The walls of the separation space, as well as the soft-magnetic or paramagnetic materials and the conductors through which the current flows and that are found within the separation space can also be provided with suitable protective layers for protection against undesirable chemical reactions, such as, e.g., corrosion. Such protective layers can be the materials that are known from materials science. Suitable are, for example, chromium platings, protective layers made of stable oxides (such as aluminum oxide), or plastic coatings (e.g., PVC, polystyrene, polyethylene). When conductors through which current flows are used inside the separation chamber to generate the magnetic gradient fields, insulation with known insulating materials (such as, e.g., plastics in the form of paint coatings) is necessary in any case.

BRIEF DESCRIPTION OF THE DRAWINGS

FIG. 6: MR angiogram of a "unfiltered" magnetite suspension.

FIG. 8: MR angiogram of a suspension filtered by a magnetic filter according to the invention.

In FIG. 1, 1 is separation space, 5 is connections (e.g., Luer locks ®), 6 is soft-magnetic iron balls, 7 is permanent magnet (ring Magnet) or electromagnet, 8 is permanent magnetic balls, 9 is soft-magnetic wall, 10 is soft-magnetic sieve, 11 is conductor through which current flows, and 12 is soft-magnetic matting (e.g., steel wool).

In FIG. 2, 1 is separation space, 6 is soft-magnetic iron balls, 7 is permanent magnet or electromagnet, 14 is infusion container, 15 is membrane filter, 16 is infusion hose, and 17 is sieve (e.g., made of metal or plastic).

In FIG. 5, 1 is permanent magnet, 2 is soft-magnetic disks with holes, 3 is inlet, and 4 is outlet.

Figure 2:
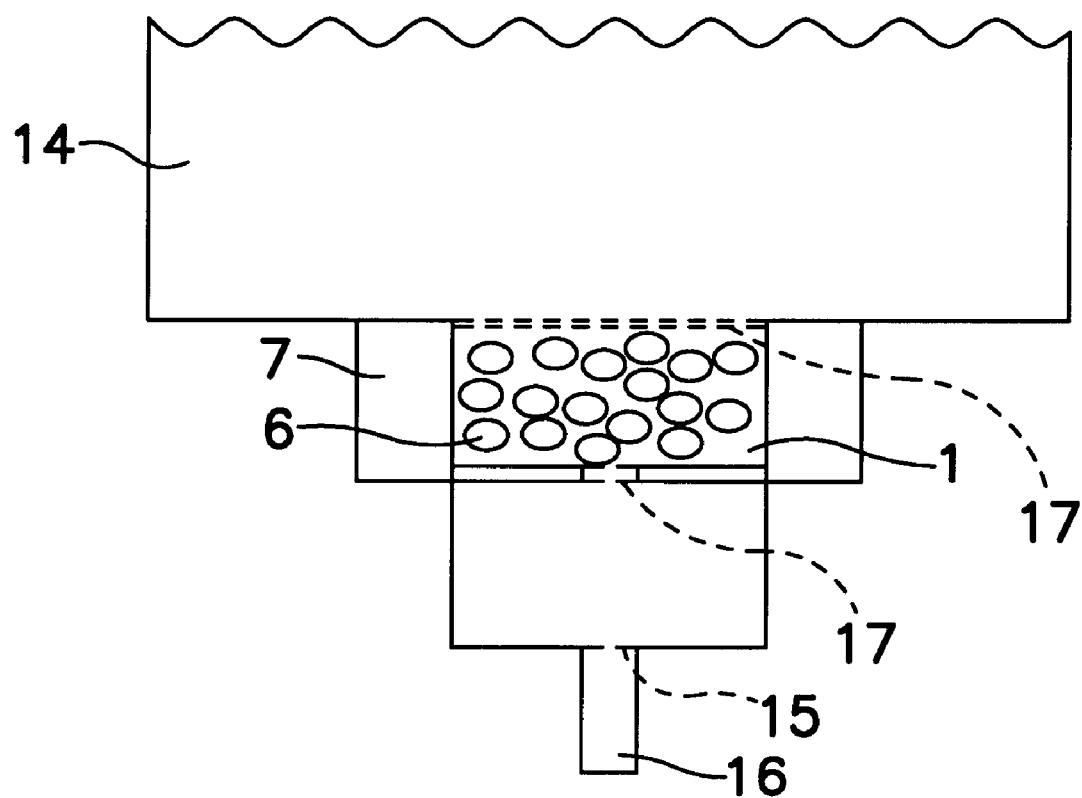
FIG. 2: Example of a device that is integrated into an infusion instrument.
Figure 3:
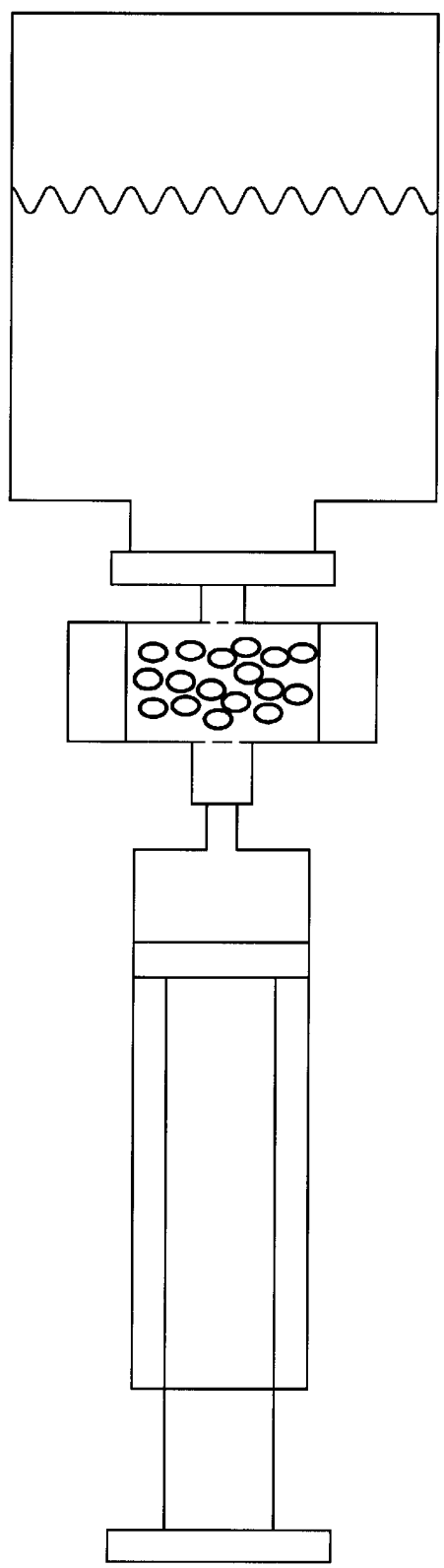
FIG. 3: Example of a device that is integrated into an infusion instrument.
Figure 4:
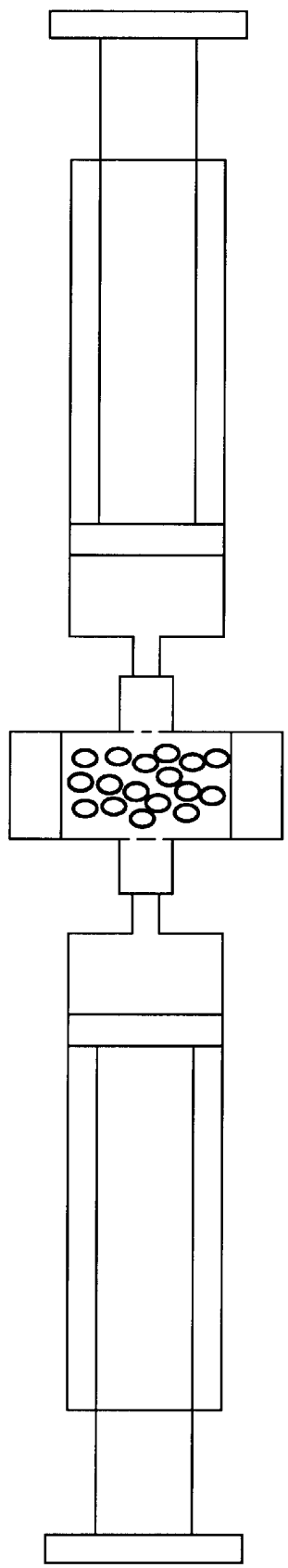
FIG. 4: Example of a device that is integrated into an infusion instrument.
Figure 5:
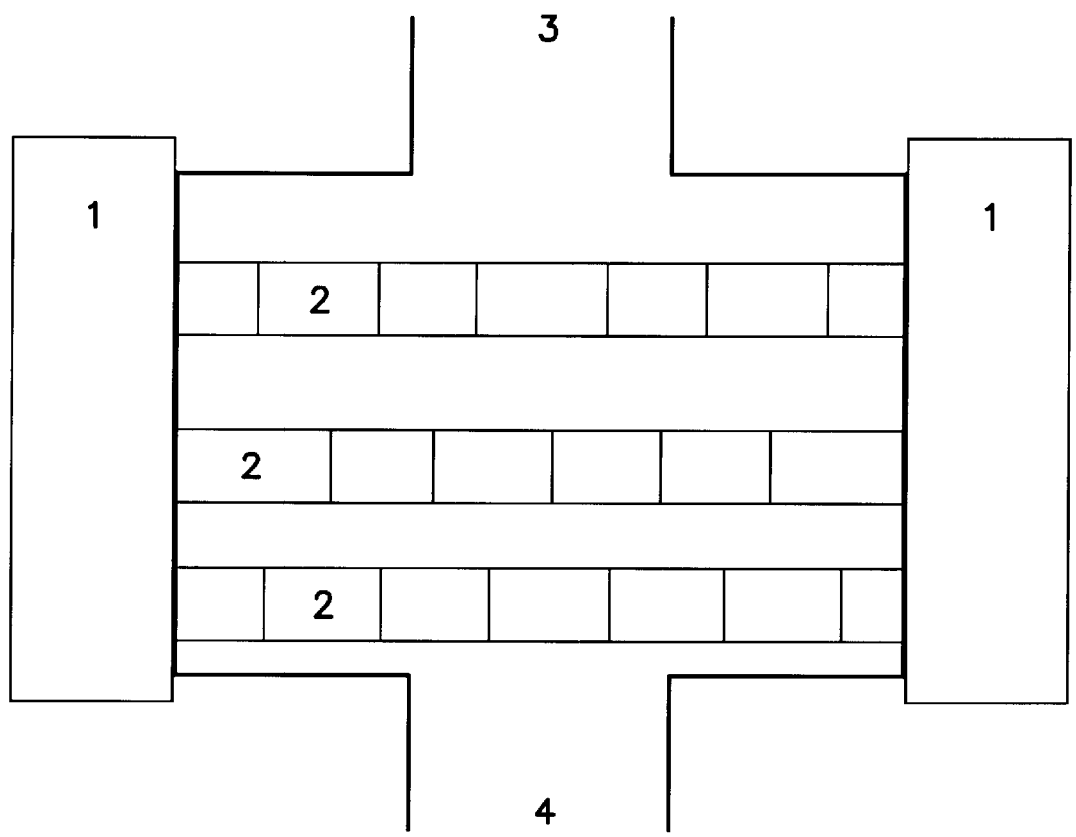
FIG. 5: Example of a device with soft-magnetic disks.

Examples of possible embodiments of the device according to the invention are shown in FIG. 1 as attachment filters. The device according to the invention can also be integrated into injection or infusion instruments. Examples of devices that are integrated into infusion instruments for magnetic separation are depicted in FIGS. 2 and 3. Another embodiment of a device that is integrated into an injection instrument is depicted in FIG. 4. The different embodiments that are outlined in FIG. 1, such as for example, the use of permanent-magnetic balls or conductors through which current flows, can be used for magnetic separation in all devices according to the invention that are integrated into infusion or injection instruments.

By the diameter of the steel disks, the number and length of the holes, which correspond to the heights of the disks or the cylinders, the rate of flow of the liquid that is to be separated and its retention time or the ratio of the liquid that is to be separated to the magnetized, wetted surface in the holes can be adjusted so that an optimum degree of separation is achieved. In addition, the rate of flow in the steel disk or in the cylinder can be reduced if several steel disks or cylinders are used one behind the other for separation and the holes of the disks or cylinders are arranged offset to one another.

Another special embodiment is obtained if the steel disks in the upper part of the separation space cannot be magnetized or consist of non-magnetized material and the disks in the lower part of the separation space are magnetized by the outer ring magnets or by a coil through which current flows. This is achieved in that magnetic particles are retained exclusively in the lower part of the separation space.

In the device according to the invention for magnetic separation of pharmaceutical preparations, it is especially advantageous that the latter can be sterilized with simple agents, such as, for example, by heat treatment, autoclaving with expanded water vapor, and gassing with ethylene oxide. In addition, said device according to the invention is much more stable than conventional membrane or pore filters. The device according to the invention can also be especially useful as a prefilter to reduce the numbers of particles before conventional filtration processes, such as, for example, sterile filtration.

Another aspect of the invention relates to the production of pharmaceutical agents, especially contrast media, which can be obtained with the aid of the device according to the invention. The device according to the invention is suitable for selecting from pharmaceutical preparations certain particles that are based on paramagnetic, superparamagnetic, ferromagnetic, or ferrimagnetic particles.

This can be done by varying the field intensity. Thus, the particles that have an especially high magnetic moment can be separated from a pharmaceutical formulation that contains a mixture of different magnetic particles (such as, e.g., a magnetite-containing suspension, as is used in magnetic resonance tomography).

Agents that contain magnetic particles are used as, for example, contrast media in nuclear spin tomography. There, i.a., suspensions based on superparamagnetic magnetites are used. Surprisingly enough, it is possible here to separate a particle mixture on the basis of, i.a., the gradient field intensity according to its magnetic moments, i.e., here the process according to the invention can be controlled in such a way that not complete deposition of the magnetic particles is accomplished, but rather selective separation, whereby especially the particles with high magnetic moments are retained.

For their purpose in diagnosis, the agents that are obtained in this case have considerably better properties, surprisingly enough, than the original particle suspensions. Thus, agents for special new applications, such as, e.g., for use as contrast media in magnetic resonance angiography or magnetic resonance lymphography, are obtained.

Thus, with the aid of the device according to the invention, influence can be exerted on the relaxation behavior of the resulting agents and thus on contrast enhancement in the MRT process. For specific medical diagnostic devices or diagnostic problems, preferably a $T_1$-relaxivity alteration, in other cases the $T_2$-relaxivity alteration (or a suitable combination of the two) of the hydrogen atoms of physiological molecules that are adjacent to the administered superparamagnetic particles is used to make a diagnosis or diagnostic picture. Via the magnetic separation, influence can also be exerted on these parameters—as also shown in the examples below.

With the aid of this device, the production of a pharmaceutical agent with altered magnetic properties from an existing pharmaceutical agent is thus possible. Since the uptake of particles introduced parenterally into humans or animals in the reticuloendothelial system (RES) depends on, i.a., their size, magnetic separation also makes it possible to exert influence on the in-vivo pharmacokinetics properties of pharmaceutical preparations. The methods known to date for controlling size distribution are unsatisfactory. The latter methods are based on expensive precipitation methods that are difficult to control in the production of pharmaceutical agent substances or on filtration processes. The latter are, as already stated, associated with immanent drawbacks.

Separation of undesirable, comparatively larger superparamagnetic particles from colloidal pharmaceutical agent preparations by centrifuging or sedimentation processes is also extremely expensive with regard to materials processing or is unsuitable for other reasons, such as, e.g., inadequate stability of the pharmaceutical agent or its formulation.

The device according to the invention is further used in separating particulate ferromagnetic or ferrimagnetic contaminants from paramagnetic pharmaceutical preparations, such as, for example, solutions of iron salts or colloidal iron dextran (e.g., iron dextran injection, USP XXV), which are used to treat iron-deficient anemias.

The examples below are used for a more detailed explanation of the object of the invention, without intending that it be limited to these examples.

EXAMPLE 1

About 100 mg of iron filings is suspended in 10 ml of an aqueous solution of 4.69 g of gadopentetic acid, dimeglumine salt. A magnetic filter, as is sketched in FIG. 1e, is built up from a ring magnet (RL 19, IBS Magnet Berlin, outside diameter 19 mm, inside diameter 6.5 mm, height 10 mm) and a separation space that is arranged in the inside volume of the ring magnet. The separation space consists of a wall made of plastic and is filled with steel wool. The suspension is flowed through the magnetic filter by hydrostatic pressure without any other force acting on it. After magnetic filtration, microscopic study can show that the iron filings are separated from the contrast medium solution by the filter.

EXAMPLE 2

Figure 1A:
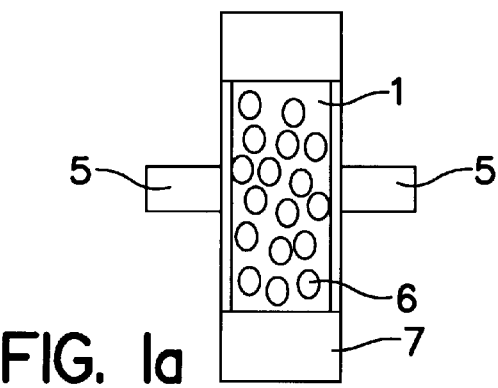
FIG. 1: Examples of various embodiments of a device according to the invention.
Figure 1B:
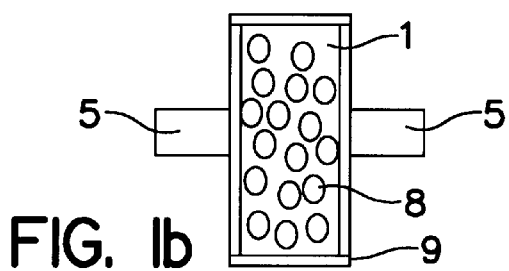
Figure 1C:
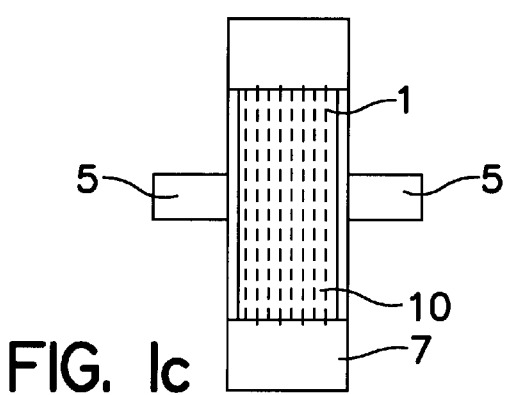
Figure 1D:
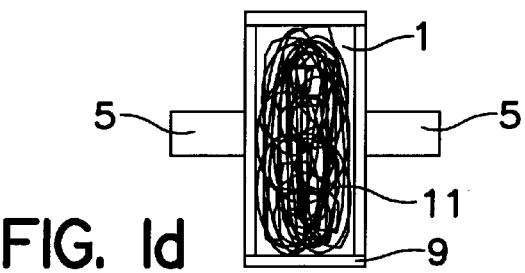
Figure 1E:
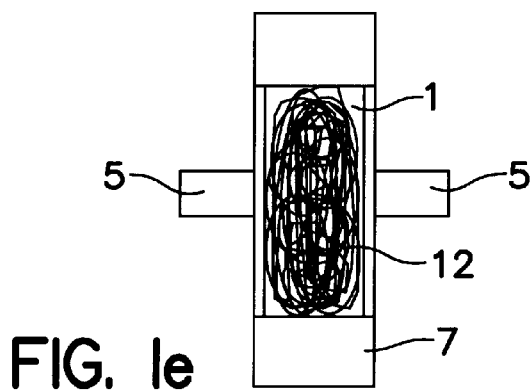

A magnetic filter, as is sketched in FIG. 1a, is built up from a ring magnet (NE 1556, IBS Magnet Berlin, outside diameter 15 mm, inside diameter 5 mm, height 6 mm) and a separation space that is arranged in the inside volume of the ring magnet. The separation space consists of a plastic wall and is filled with iron shot balls (diameter of about 0.3 mm). 0.8 ml of a superparamagnetic colloidal solution of iron oxide nanoparticles (produced according to U.S. Pat. No. 4,101,435; Example 7) with an iron content of 500 mmol/l and a $T_2$-relaxivity ($r_2$) of about 160 l/(mmol s) is filtered through the magnetic filters under the action of hydrostatic pressure. The $T_2$-relaxivity ($r_2$) of the filtrate is about 60 l/(mmol s).

As a ratio of relaxivities $r_2/r_1$, a value of 7.4 was determined for the untreated solution, while a value of 3.2 was measured for the filtrate.

All MR angiograms (FIGS. 6–8) were recorded on an experimental MRT (SISCO SIS 85, 2.0 Tesla) using A 3 D FLASH technology (10/2, 6/40°).

As test animals, anesthetized (Rompun®/Ketavet®, mixture 1:1) rats (Han. Wistar; ~200 g of body weight) were used.

Both with the "unfiltered" starting substance and with the preparation that is "filtered" according to the invention, first in each case a precontrast picture was prepared, as well as pictures taken 1, 15, or 30 minutes after intravenous administration of the respective contrast medium. In this case, a dose of about 100 μmol of iron/kg of body weight was always used.

FIG. 6 shows the MR angiogram of the "unfiltered" magnetite suspension. The contrast effect that is achieved after 1 minute or 15 minutes is of little diagnostic informational value.

Figure 7A:
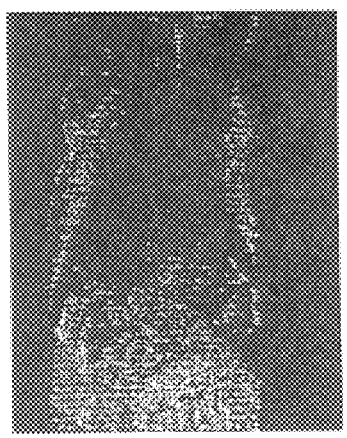
FIG. 7: MR angiogram of a "filtered" magnetic suspension.
Figure 7B:
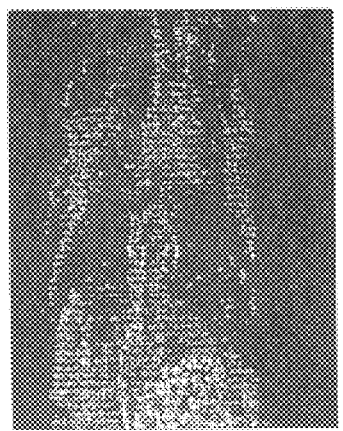
Figure 7C:
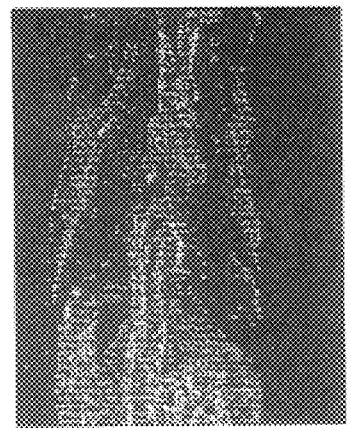

FIG. 7 shows the MR angiogram of the "filtered" magnetite suspension [(a) precontrast, (b) 1 min p.i.), (c) 30 minutes p.i.]. Here, even after one minute, a large number of vessels can be clearly detected; the effect increases dramatically 30 minutes after administration of the contrast medium. The contrast medium preparation that is prepared according to the invention is extremely well suited for magnetic resonance angiography compared to the untreated substance.

EXAMPLE 3

A magnetic filter, as is sketched in FIG. 1a, is built up from a ring magnet (NE 2016, IBS Magnet Berlin, outside diameter 20 mm, inside diameter 10 mm, height 6 mm) and a separation space that is arranged in the inside volume of the ring magnet. The separation space consists of a wall made of plastic and is filled with iron shot balls (diameter about 0.3 mm). 0.8 ml of a superparamagnetic colloidal solution of iron oxide nanoparticles (produced in U.S. Pat. No. 4,101,435; Example 7) with an iron content of 500 mmol/l and a $T_2$-relaxivity ($r_2$) of about 160 l/(mmol s) is filtered through the magnetic filters under the action of hydrostatic pressure. The ratio of relaxivities $r_2$ and $r_1$ is, with the filtrate, $r_2/r_1=2.1$.

The angiograms that are obtained with this preparation are shown in FIG. 8, whereby even after one minute, a differentiation of the vessels can be detected, as is achieved only at a considerably later time in the case of the preparation that is produced according to Example 2.

What is claimed is:

1. A method of preparing a contrast medium useful for angiography or lymphography comprising filtering with a magnetic filter a suspension of coated magnetic particles whose ratio of relaxivities $r_2/r_1$ is greater than 3.2 before filtering, and separating magnetic particles whose ratio of relaxivities $r_2/r_1$, is 3.2 or lower.

2. A method of preparing a contrast medium according to claim 1 wherein the magnetic particles are paramagnetic, superparamagnetic, ferromagnetic, or ferrimagnetic particles.

3. A method of claim 2 wherein the particles are superparamagnetic particles.

4. A method of preparing a contrast medium according to claim 3 wherein said ratio of relaxivities of the magnetically separated coated magnetic particles is less than 2.1.

5. A method of claim 4 wherein said ratio of relaxivities of the magnetically separated coated magnetic particles is less than 1.

6. A method of taking an MRI angiography or lymphography image of a patient comprising administering the coated magnetic particles prepared by the process of claim 1.

7. A method of taking an MRI angiography or lymphography image of a patient comprising administering the coated magnetic particles prepared by the process of claim 4.

8. A method of taking an MRI angiography or lymphography image of a patient comprising administering the coated magnetic particles prepared by the process of claim 5.

* * * * *